United States Patent
Hansel et al.

(10) Patent No.: US 6,255,109 B1
(45) Date of Patent: Jul. 3, 2001

(54) NITRIC OXIDE-SCAVENGING SYSTEM FOR CULTURING OOCYTES, EMBRYOS, OR OTHER CELLS

(75) Inventors: William Hansel, Baton Rouge, LA (US); Jeong-Mook Lim, Seoul (KR)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/335,244

(22) Filed: Jun. 17, 1999

Related U.S. Application Data
(60) Provisional application No. 60/155,236, filed on Jun. 24, 1998, now abandoned.

(51) Int. Cl.$^7$ .................................................. C12N 5/06
(52) U.S. Cl. ............................ 435/373; 435/404; 435/408
(58) Field of Search .................................... 435/373, 404, 435/408

(56) References Cited

FOREIGN PATENT DOCUMENTS
9527040  * 10/1995 (WO).

OTHER PUBLICATIONS

Dawson et al., PNAS USA 88: 6368–6371 (Jul. 1991).*
Juretic et al., Cellular Immunology 157: 462–477 (1994).*
Dekel et al., Endocrinology 98(2): 498–504 (1976).*
Eyestone, W. et al., "Co–culture of Early Cattle Embryos to the Blastocyst Stage with Oviductal Tissue or in Conditioned Medium," J. Reprod. Fert. 85:715–720 (1989).
Fukuda, A. et al., "Production of nitric oxide from mouse embryo and effect of nitrite on mouse embryonic development in vitro," Biol Reprod 54:173 (abstr) (1996) Reprod. Fertil. Dev. 8:1199–1205 (1996).
Gouge, R.C. et al., "Nitric Oxide as a Regulator of Embryonic Development," Biology of Reproduction, v.58, pp. 875–879 (1998).
Haddad, E. et al., "Early embryo loss is associated with local production of nitric oxide by decidual mononuclear cells," J. Exp. Med., 182, 1143–1151 (1995).
Jablonka–Shariff, A. et al., "Hormonal Regulation of Nitric Oxide Synthases and Their Cell–Specific Expression during Follicular Development in the Rat Ovary," Endocrinology 138:460–468 (1997).
Katušić, Z. et al., "Nitric Oxide Synthase: From Molecular Biology to Cerebrovascular Physiology," NIPS 9:64–67 (1994).
Lim, J. et al., "A Continuous Flow, Perifusion Culture System for 8–to 16–Cell Bovine Embryos Derived from In Vitro Culture," Theriogenology 46:1441–1450 (1996).
Lim, J. et al., "A Serum–Free Medium for Use in a Cumulus Cell Co–Culture System for Bovine Embryos Derived from In Vitro Maturation and In Vitro Fertilization," Theriogenology 45:1081–1089 (1996).
Lim, J. et al., "Intracytoplasmic glutathione concentration and the role of β–mercaptoethanol in preimplantation development of bovine embryos," Theriogenology, 46, 429–439 (1996).
Lim, J. et al., "Perifusion Culture System for Bovine Embryos: Improvement of Embryo Development by Use of Bovine Oviduct Epithelial Cells, and Antioxidant and Polyvinyl Alcohol," Reprod. Fertil. Dev., 9:411–418 (1997).
Lim, J. et al., "Roles of growth factors in the development of bovine embryos fertilized in vitro and cultured singly in a defined medium," Reprod. Fertil. Dev., 8, 1199–1205 (1996).
McCann, S. et al., "The Role of Nitric Oxide in Reproduction," Soc. For Experimental Biology and Medicine, pp. 7–15 (1996).
McDonald, L. et al., "Nitric Oxide and Cyclic GMP Signaling," Soc. For Experimental Biology and Medicine, pp. 1–6 (1996).
Novaro et al., "Nitric oxide synthase regulation during embryonic implantation," Reprod. Fertil. Dev. 9:557–564 (1997).
Thibodeaux, J. et al., "Stimulation of Development of In Vitro–Matured and In Vitro–Fertilized Bovine Embryos by Platelets," J. Anim. Sci. 71:1910–1916 (1993).
Thibodeaux, J. et al., "Role of Platelet–Derived Growth Factor in Development of in vitro Matured and in vitro Fertilized Bovine Embryos," J. Reprod. Fert. 98:61–66 (1993).
Vega, M. et al., "Expression of Nitric Oxide Synthase (NOS) in Human Corpus Luteum (hCL) and the Role of Nitric Oxide (NO) on Luteal Steroidogenesis" (abstract), Biol. Reprod., 54 (Suppl. 1):66 (1996).

* cited by examiner

*Primary Examiner*—Jean C. Witz
(74) *Attorney, Agent, or Firm*—John H. Runnels

(57) ABSTRACT

Nitric oxide adversely affects survival and development of cells such as oocytes and embryos in vitro, particularly in a co-culture system. The addition of a nitric oxide inhibitor such as hemoglobin to such systems eliminates this toxic effect, and promotes mammalian oocytes, embryos, or other cells in vitro.

10 Claims, No Drawings

NITRIC OXIDE-SCAVENGING SYSTEM FOR CULTURING OOCYTES, EMBRYOS, OR OTHER CELLS

The benefit of the Jun. 24, 1998 filing date of provisional application 60/155,236 is claimed under 35 U.S.C. §119(e).

This invention pertains to compositions and methods for mammalian cell culture in vitro, for example the culture of mammalian oocytes or embryos.

The development of this invention was partially supported by a HATCH grant from the United States Department of Agriculture. The Government has certain rights in this invention.

Embryo Cell Culture Media

Various cell culture media have been used to support the growth of mammalian cells in vitro. Many of these media are quite satisfactory in supporting the growth of certain cell types. Other cell types, however, have proven more difficult to support in vitro. There is a continuing need for improved media to support the growth of such cell types.

There is a particular need for improved media to support mammalian oocytes and embryos. A high percentage of embryos that are fertilized or transferred in vitro cease development prematurely. The consequences are felt at both the economic and the human levels.

In the livestock industry, the value of in vitro-fertilized (IVF) embryos from genetically superior stock can be very high. Significant economic savings will result from methods that reduce the high rate of loss of bovine embryos.

Many forms of fertility treatments for humans involve the in vitro fertilization or transfer of oocytes or embryos. The success rates of human fertility treatments are not high. The low success rates impose substantial economic and emotional costs. Even incremental improvements in the success rate can be of substantial benefit. One of the many causes of the low overall success rate is the frequent failure of embryos to grow and develop properly in vitro. Improved media to better support embryo growth can not only enhance the success rate of fertility treatments, but ironically can also reduce the rate of multiple pregnancies resulting from the treatments. Because the overall success rate of current methods is low, practitioners often implant multiple embryos to increase the likelihood of pregnancy. Implanting multiple embryos increases the likelihood of multiple pregnancies as well. If each individual embryo were more likely to survive, then the perceived need to implant multiple embryos simultaneously would decline, and the rate of multiple pregnancies would decrease.

The development of bovine embryos has been supported by media containing inorganic salts, amino acids, carbohydrates, growth factors, and antioxidants. Development has been enhanced by co-culturing embryos with reproductive tissue cells and complex media containing sera and macromolecules. However, embryotoxic substances in these co-culture systems can interfere with the development of embryos. For example, it has been reported that ammonium and purines in the culture system have an embryotoxic effect on the pre-implantation development of bovine and murine embryos. Thus despite some improvements, the overall rate of successful development of embryos in vitro remains low. There is a continuing, unfilled need for improved media for the culture or co-culture of oocytes and embryos.

In vitro fertilization (IVF) and embryo transfer (ET) techniques for bovine oocytes and embryos have been used for both commercial and research purposes. Similar techniques have been used in infertility treatments for humans. Although several researchers have achieved high IVF success rates (~90%), only a small proportion (~20%) of in vitro fertilized zygotes develop to the morula and blastocyst stages. A large number of inseminated zygotes cultured in vitro cease development at the 8- to 16-cell stage, a time corresponding to embryonic genome activation. Relatively few morulae or blastocysts derived from IVF are suitable for ET.

Papers disclosing in vitro culture and co-culture systems for oocytes and embryos include the following: J. Lim et al., "Roles of Growth Factors in the Development of Bovine Embryos Fertilized in vitro and Cultured Singly in a Defined Medium," Reprod. Fertil. Dev., 8:1199–1205 (1996); W. Eyestone et al., "Co-culture of Early Cattle Embryos to the Blastocyst Stage with Oviductal Tissue or in Conditioned Medium," J. Reprod. Fert. 85:715–720 (1989); J. Thibodeaux et al., "Role of Platelet-Derived Growth Factor in Development of in vitro Matured and in vitro Fertilized Bovine Embryos," J. Reprod. Fert. 98:61–66 (1993); J. Thibodeaux et al., "Stimulation of Development of In Vitro-Matured and In Vitro-Fertilized Bovine Embryos by Platelets," J. Anim. Sci. 71:1910–1916 (1993); J. Lim et al., "A Serum-Free Medium for Use in a Cumulus Cell Co-Culture System for Bovine Embryos Derived from In Vitro Maturation and In Vitro Fertilization," Theriogenology 45:1081–1089 (1996); J. Lim et al., "Intracytoplasmic Glutathione Concentration and the Role of β-Mercaptoethanol in Preimplantation Development of Bovine Embryos," Theriogenology 46:429–439 (1996); J. Lim et al., "A Continuous Flow, Perifusion Culture System for 8- to 16-Cell Bovine Embryos Derived from In Vitro Culture," Theriogenology 46:1441–1450 (1996); and J. Lim et al., "Perifusion Culture System for Bovine Embryos: Improvement of Embryo Development by Use of Bovine Oviduct Epithelial Cells, and Antioxidant and Polyvinyl Alcohol," Reprod. Fertil. Dev., 9:411–418 (1997).

Nitric Oxide

The nitric oxide (NO) molecule controls a wide range of biological activities, including programmed cell-death (apoptosis), activation of guanylyl cyclase, interaction with superoxide anions to form peroxynitrite, regulation of glycolysis by modification of glyceraldehyde-3-phosphate dehydrogenase activity, control of the mitochondrial transport electron chain, the citric acid cycle, DNA synthesis, binding to the iron-sulphur center of enzymes, stimulation of ADP-ribosylation of proteins, production of arachidonic acid metabolites such as prostaglandin E2 and 5-hydroxyeicosatetraenoic acid, sperm motility and viability, and capacitation and hyperactivation of spermatozoa in vitro.

NO plays an important role in the regulation of various aspects of cell metabolism. During human pregnancy, NO is produced in the placenta, the decidua, and the endometrium. It has been reported that NO synthesis increases during pregnancy but decreases toward the end of gestation. A peak in NO synthesis has also been reported in the rat uterus during pregnancy. See Novaro et al., "Nitric oxide synthase regulation during embryonic implantation," Reprod. Fertil. Dev. 9:559–564 (1997). Early embryonic loss has been associated with local production of NO by decidual cells in the mouse uterus. See E. Haddad et al., "Early embryo loss is associated with local production of nitric oxide by decidual mononuclear cells," J. Exp. Med., 182, 1143–1151 (1995).

Papers discussing nitric oxide and its role in reproductive biology include the following: L. McDonald et al., "Nitric Oxide and Cyclic GMP Signaling," PSEBM, 211:1–6 (1996); S. McCann et al., "The Role of Nitric Oxide in Reproduction," PSEBM, 211:7–15 (1996); Z. Katušić et al., "Nitric Oxide Synthase: From Molecular Biology to Cerebrovascular Physiology," NIPS 9:64–67 (1994); A. Jablonka-Shariff et al., "Hormonal Regulation of Nitric Oxide Synthases and Their Cell-Specific Expression during Follicular Development in the Rat Ovary," Endocrinology 138:460–468 (1997); and M. Vega et al., "Expression of Nitric Oxide Synthase (NOS) in Human Corpus Luteum (hCL) and the Role of Nitric Oxide (NO) on Luteal Steroidogenesis" (abstract), Biol. Reprod., 54 (Suppl. 1):66 (1996).

A. Fukuda et al., "Production of nitric oxide from mouse embryo and effect of nitrite on mouse embryonic development in vitro," Biol Reprod 54:173 (abstr) (1996) reported that NO may have a regulatory role in preimplantation embryonic development in the mouse.

Hemoglobin (Hb) is widely known as the iron-containing molecule in red blood cells responsible for the transport of oxygen and carbon dioxide. It has recently been recognized that hemoglobin also binds nitric oxide with high affinity. Hemoglobin has been used in some experimental systems as a "sink" for nitric oxide that diffuses outside the cell during a process being studied.

The Invention

We have discovered that nitric oxide adversely affects the development of certain cells in vitro, such as the pre-implementation development of oocytes and embryos, particularly in a co-culture system. It has not previously been suggested that NO can be toxic in such systems. We have also discovered that the addition of a nitric oxide inhibitor such as hemoglobin to such systems eliminates this toxic effect, and promotes the maintenance, growth, and development of cells such as oocytes and embryos.

As is true of many other culture media, the standard embryo culture medium that we have used in our laboratory recently, modified bovine embryo culture medium (mBECM; J. Lim et al., Roles of growth factors in the development of bovine embryos fertilized in vitro and cultured singly in a defined medium. Reprod. Fertil. Dev. 8:1199–1205 (1996)), contains L-arginine (63.2 mg/L), which is a substrate for NO synthesis. (Arginine is normally included in the medium as it is has a variety of effects on cell metabolism, and is beneficial to the growth of embryos. Co-culture cells and serum can also be sources of arginine.) Thus embryos cultured in this medium may be able to synthesize NO for various biological events, as may cells such as cumulus-granulosa cells (CGs) used in embryo co-culture systems. We have found that, whatever its origin, NO in the culture medium can adversely affect embryonic development.

We have investigated the role of NO in the development of IVF bovine embryos up to the blastocyst stage. In a series of experiments, we examined the effects of adding a spontaneous NO releaser (sodium nitroprusside; SNP) and an NO scavenger (hemoglobin; Hb), to co-culture systems. In addition to these experiments, we also measured NO metabolites in both developing embryos and in developmentally arrested embryos. In other experiments, we attempted to determine whether CGs are responsible for the NO, and to determine the critical time in early embryonic development at which NO exerts its effects.

Following is a brief summary of the experimental methods and results reported in greater detail below.

In Example 1, embryos were cultured in a cumulus-granulosa cell (CG) co-culture system to which 0.008 or 0.04 mM of sodium nitroprusside (SNP), a spontaneous NO releaser, was added at 18 or 60 h post-insemination. Embryonic development was greatly ($P<0.001$) inhibited by the addition of SNP, regardless of the time of SNP addition and regardless of the SNP concentration. In Example 2, 8-cell embryos were cultured singly in a defined medium, to which 0.0016, 0.008 or 0.04 mM of SNP was added. Development to the blastocyst stage greatly ($P<0.001$) decreased after addition of SNP, compared with controls. A higher ($P<0.02$) concentration of NO metabolites was found in developmentally-arrested embryos than in developing embryos at 144 h post-insemination (Example 3). In Example 4, embryos co-cultured with CGs reached the blastocyst stage at a significantly higher rate ($P<0.02$) after addition of hemoglobin (Hb, 1 μg/ml). Pre-hatching development of embryos increased significantly ($P<0.05$) after addition of Hb at different time intervals (18, 60, or 144 h post-insemination) in Example 5. ("Hatching" refers to the point in development when the cytoplasm of the embryo increases to the point at which it breaks through its "outer membrane," the zona pellucida.) In the absence of CGs, embryonic development was not enhanced by adding Hb to the culture medium (Example 6). Pre-hatching development of 8-cell embryos derived from a Hb-containing culture system was not promoted by the further addition of Hb after transfer of the embryos to a defined and CG-free single-embryo culture system (Example 7). We concluded that NO, which may be secreted from CGs, inhibits the pre-hatching development of mammalian embryos fertilized in vitro, and that the use of an NO scavenger, Hb, in a co-culture system enhanced blastocyst formation.

We evaluated whether the effect of Hb on embryonic development was influenced by the time of the year (Example 8). In Example 9, we tested whether addition of an NO synthesis inhibitor, $N^G$-Lω-nitro-L-arginine methyl ester hydrochloride (L-NAME), further augmented the positive effect of Hb. Bovine IVF-oocytes were used in our experimental models. In Examples 8 and 9, bovine IVF oocytes were cultured in modified bovine embryo culture medium (mBECM) supplemented with either hemoglobin (Hb, 1 μg/ml) or L-NAME (1 or 1000 nM) in a cumulus-granulosa cell co-culture system. In Example 8, a total of 1,675 cumulus-oocyte/zygote complexes were collected during a 9-month period and cultured to the blastocyst stage in mBECM, with or without Hb, after in vitro maturation and IVF. The effects of Hb addition and month of oocyte collection on embryonic development were significant ($P<0.0024$). Seasonal variation ($P<0.0023$) was detected in all developmental stages. However, addition of Hb to mBECM consistently enhanced embryonic development to the morula and blastocyst stages, regardless of the month. No significant differences were found in the interaction between Hb addition and month, except for the cleavage rate. Overall, a greater percentage of embryos developed to the 8-cell ($P<0.0459$), 16-cell ($P<0.001$), morula ($P<0.0013$), and blastocyst ($P<0.0024$) stages after addition of Hb than after no addition. In Example 9, addition of L-NAME to MBECM, supplemented with Hb, did not further stimulate pre-hatching development. The promoting effect of Hb on in vitro development of embryos was found to be highly repeatable over an extended period of time.

Materials and Methods

Examples 1–7

Composition of Media (Examples 1–7)

The basic medium used for maturation of oocytes was tissue culture medium (TCM)-199 with Earle's salts buffered with 25 mM HEPES (Gibco BRL, Grand Island, N.Y.), supplemented with 10% (v/v) heat-inactivated fetal bovine serum (FBS; Hyclone Laboratories, Logan, UT), 1 μg/ml estradiol-17β (NOBL Laboratories, Sioux Center, Iowa), 3 μg/ml bovine FSH (NOBL Laboratories), 6 μg/ml bovine LH (NOBL Laboratories), and 25 μg/ml gentamycin (Sigma Chemical Co., St. Louis, Mo.). The basic medium used for treatment of spermatozoa and fertilization of oocytes was a modified Tyrode's medium (J. Parrish et al., Capacitation of bovine sperm by heparin. Biol. Reprod. 38, 1171–1180 (1988)), supplemented with 0.25 mM sodium pyruvate (Gibco BRL), 6 mg/ml fatty acid (FA)-free BSA (No. A-6003, Sigma), 15 μg/ml calcium heparin from porcine intestinal mucosa (183 USP/mg; H-8398, Sigma) and 25 μg/ml gentamycin.

mBECM containing 10 μM β-mercaptoethanol was used to culture embryos, as described in J. Lim et al., "Roles of growth factors in the development of bovine embryos fertilized in vitro and cultured singly in a defined medium," Reprod. Fertil. Dev., 8, 1199–1205 (1996). To culture individual 8-cell embryos we used mBECM supplemented with 1 ng/ml platelet derived growth factor type AB (PDGF;

Upstate Biotechnology Inc., Lake Placid, N.Y.), 1 ng/ml transforming growth factor-β (TGF; R & D System, Minneapolis, Minn.), 50 ng/ml arachidonic acid (AA; Cayman Chemical Co., Ann Arbor, Mich.), 100 μM glutathione (GSH; Sigma Co.) and 1 mg/ml polyvinyl alcohol (PVA) (mBECM-S). mBECM to which 10% (v/v) FBS was added (mBECM-C) was used for co-culturing inseminated zygotes with CGs and for producing 8-cell embryos. Osmolarity of the medium was maintained within the range of 265–290 mOsm.

In vitro-Maturation, -Fertilization, and -Culture (Examples 1–7)

The bovine cumulus-oocyte complexes (COCs) used were collected in Madison, Wis. (BOMED, Inc.), and were shipped in 2-ml of maturation medium in a battery powered incubator via overnight express mail service. Oocytes matured during transit and arrived within 24 h after exposure to maturation medium, pre-equilibrated at 39° C. in 5 % $CO_2$ in air. At 22–24 h after exposure to the medium, the COCs were inseminated in vitro as described in J. Lim et al., "Intracytoplasmic glutathione concentration and the role of β-mercaptoethanol in preimplantation development of bovine embryos," *Theriogenology*, 46, 429–439 (1996). At 18 h post-insemination, COCs were cultured in groups (30–35 embryos) in a 4-well multidish (Nunc, Roskilde, Denmark) containing 0.8-ml of mBECM-C. Embryos were dislodged from CGs at 36–48 h post-insemination.

Measurement of NO Metabolites in Embryos and Media Conditioned with CGs (Examples 1–7)

Concentrations of the primary NO metabolites (nitrate and nitrite) in embryos were measured by enzyme linked immunosorbent assay (ELISA) using the protocol of Cayman's nitrate/nitrite kit (Cat. No. 780001, Cayman Co.). Briefly, collected embryos were placed in 10 ml of mBECM supplemented with 1 mg/ml PVA and stored at –80° C. until assayed. After thawing at room temperature (20 to 25° C.), the embryos were homogenized by ultrasonication. Embryo suspensions were treated with nitrate reductase for 3 h to convert nitrate to nitrite, and then treated with Gries' reagents for 10 min. Total nitrite concentrations of the samples were measured by absorbance at 540 nm using a plate reader (Spectra-III, SLT Labinstrument, Vienna, Austria).

Experimental Design (Examples 1–7)

In Example 1, embryos (83–85 per group) collected 18 h post-insemination were cultured in mBECM-C, to which 0, 0.008, or 0.04 mM SNP was added at 18 or 60 h post-insemination. In Example 2, 8-cell embryos (80 per group) were produced in a co-culture system containing CGs and mBECM-C, and then beginning at 60 h post-insemination were cultured singly in a defined culture medium (mBECM-S), to which 0, 0.0016, 0.008, or 0.04 mM of SNP (S-0501, Sigma Co.) was added. In Example 3 embryos, either uncleaved (n=99) or developed to the 2-cell stage (90), were collected 48 h post-insemination; and cleaved embryos, either developed to the morula stage (69) or degenerate (63) were collected 144 h post-insemination. NO metabolites were then measured in the embryos. In Example 4, three groups of 95 zygotes each were co-cultured with CGs in mBECM-C, to which 0, 1, or 10 μg/ml Hb (bovine, mainly methemoglobin, H-2500, Sigma Co.) was added. Since our experiments showed that NO inhibits early bovine embryonic development, and that Hb protects against NO action, in Example 5 we attempted to determine the critical times at which Hb exerts a protective effect. Inseminated oocytes (104 per group) were co-cultured with CGs in mBECM-C up to 192 h post-insemination; and Hb (1 μg/ml) was added to the medium at 18, 60, or 144 h post-insemination. In Example 6, inseminated oocytes (93 per group) were cultured in the presence or absence of CGs in mBECM-C to which either 0 or 1 μg/ml Hb was added. In Example 7, 8-cell embryos (100 per group), obtained after culture in mBECM-C supplemented with Hb (1 μg/ml), were cultured singly in mBECM-S, with or without Hb.

Statistical Analyses (Examples 1–7)

Oocytes or 8-cell embryos were randomly and equally allocated to each treatment group. In Examples 1, 2, and 4–7, oocytes or embryos that had developed to the 2-cell, 8-cell, >8-cell, 16-cell, morula, and blastocyst stages were individually scored '1' (developed) at 48, 60, 96, 120, 144 and 192 h post-insemination, respectively. Oocytes or embryos that did not develop to these stages at the same times were scored '0' (non-developed). Sums of the scores in each stage of development were evaluated by analysis of variance (ANOVA) using the general linear model (PROC-GLM) in the SAS program software. In Example 3, concentrations of NO metabolites in embryos were subjected to ANOVA. Where an experimental parameter was found to be significant, the effects of SNP (Examples 1 and 2), developmental status of embryo (Example 3), Hb (Examples 4–7), and CG (Example 6) were compared by the least squares method. Differences were regarded as statistically significant where P values were less than 0.05.

Results, Example 1

Addition of SNP was found to significantly (P<0.001) affect the percentage of embryos developing to the blastocyst stage (Table 1). When SNP was added at 18 h post-insemination, embryonic development to the 8-cell stage was significantly (P<0.004) inhibited (51% vs. 0–31%), regardless of SNP concentration. Addition of SNP at 60 h post-insemination also inhibited embryonic development to the blastocyst stage, and the proportion of blastocysts significantly (P<0.001) decreased after the addition of 0.008 or 0.04 mM SNP (0–8%) compared with controls (23%). Embryonic development was immediately blocked by the addition of 0.04 mM SNP and, compared with control, a decrease in the proportions of 2-cell and 16-cell embryos was found after addition of 0.04 mM SNP at 18 h (77 vs. 0%; P<0.001) and 60 h (39 vs. 24%; P<0.02) post-ins respectively.

TABLE 1

Results of Example 1: Effects of the Addition of Sodium Nitroprusside (SNP, 0.008 or 0.04 mM) to mBECM-C Containing FBS on the Pre-hatching Development of Inseminated Oocytes (83–85 per Group)

| Time of addition (hr post-insemination) | Concentrations of SNP (mM) | No. of oocytes cultured | NUMBER AND (%) OF EMBRYOS DEVELOPED TO | | | | |
|---|---|---|---|---|---|---|---|
| | | | 2-cell[a] | 8-cell[a] | 16-cell[a] | Morula[a] | Blastocyst[a] |
| No addition | — | 83 | 67 (77)[b] | 42 (51)[b] | 32 (39)[b] | 26 (31)[b] | 19 (23)[b] |
| 18 | 0.008 | 85 | 63 (74)[b] | 26 (31)[c] | 19 (22)[c] | 10 (12)[c] | 0 (0)[c] |
| 18 | 0.04 | 85 | 0 (0)[c] | 0 (0)[d] | 0 (0)[d] | 0 (0)[d] | 0 (0)[c] |

TABLE 1-continued

Results of Example 1: Effects of the Addition of Sodium Nitroprusside
(SNP, 0.008 or 0.04 mM) to mBECM-C Containing FBS on the Pre-hatching
Development of Inseminated Oocytes (83–85 per Group)

| Time of addition (hr post-insemination) | Concentrations of SNP (mM) | No. of oocytes cultured | NUMBER AND (%) OF EMBRYOS DEVELOPED TO | | | | |
|---|---|---|---|---|---|---|---|
| | | | 2-cell[a] | 8-cell[a] | 16-cell[a] | Morula[a] | Blastocyst[a] |
| 60 | 0.008 | 84 | 63 (75)[b] | 42 (50)[b] | 29 (35)[b] | 25 (30)[b] | 7 (8)[d] |
| 60 | 0.04 | 85 | 68 (80)[b] | 44 (52)[b] | 20 (24)[c] | 0 (0)[d] | 0 (0)[e] |

[a]Development to the 2-cell, 8-cell, 16-cell, morula, and blastocyst stages was examined at 48, 60, 96, 144, and 192 hours post-insemination, respectively.
[b,c,d]Values with different superscripts within each column are significantly different, $P < 0.05$.

Results, Exanple 2

Addition of SNP to mBECM-S significantly ($P<0.001$) reduced the number of 8-cell embryos developing to the 16-cell, morula, and blastocyst stages. As shown in Table 2, the number of blastocysts greatly ($P<0.001$) decreased after addition of 0.0016, 0.008, or 0.04 mM SNP (0–3%) compared with control (18%). Development beyond the 8-cell and to the 16-cell and morula stages also decreased ($P<0.006$) following addition of 0.04 mM SNP compared to all other concentrations (29% vs. 58–63% in >8-ell, 4% vs. 39–41% in 16-cell, and 0% vs. 16–33% in morula).

TABLE 2

Results of Example 2: Effects of the Addition of Sodium
Nitroprusside (SNP, 0.0016, 0.008 or 0.04 mM) to mBECM-S Containing
Platelet-Derived Growth Factor, Transforming Growth Factor,
Arachidonic Acid, Glutathione, Mercaptoethanol, and Polyvinyl Alcohol
on the Pre-hatching Development of 8-Cell Embryos (80 per Group)
Cultured Singly

| SNP Concentration (mM) | No. of oocytes cultured | Percent of Embryos Developed to: | | | |
|---|---|---|---|---|---|
| | | >8-cell | 16-cell | Morula | Blastocyst |
| 0 | 80 | 59[a] | 41[a] | 33[a] | 0[a] |
| 0.0016 | 80 | 58[a] | 41[a] | 23[a] | 3[b] |
| 0.008 | 80 | 63[a] | 39[a] | 16[bc] | 1[b] |
| 0.04 | 80 | 29[b] | 4[b] | 0[c] | 0[b] |

[a,b,c]Values with different superscripts within each column are significantly different, $P < 0.05$.

Results, Example 3

There was no significant ($P>0.9$) difference in the concentrations of NO metabolites in embryos developed to the 2-cell stage and uncleaved embryos (average embryonic NO level, 0.55–0.58 $\mu$M) at 48 h post-insemination. As shown in Table 3, however, an increase ($P<0.02$) in the concentration of NO metabolites was seen in degenerate embryos (1.28±0.16 $\mu$M/embryo) compared to embryos developed to the morula stage (0.59±0.16 $\mu$M/embryo) at 144 h post-insemination.

TABLE 3

Results of Example 3:
Concentrations of Nitric Oxide Metabolites in Embryos either Cleaved
(90) or not Cleaved (99) at 48 h; and in Cleaved Embryos Developed
or to the Morula Stage (69) or degenerate (63) at 144 h post-insemination

| | Developing Embryos, 48 hours | Degenerate Embryos, 48 hours | Developing Embryos, 144 hours | Degenerate Embryos, 144 hours |
|---|---|---|---|---|
| Average embryonic concentration of NO metabolites, $\mu$M | 0.58 ± 0.26 | 0.55 ± 0.22 | 0.59 ± 0.16 | 1.28* ± 0.16 |

*Value significantly different from other entries, $P < 0.02$.

Results, Example 4

The presence of Hb in the serum-containing medium (mBECM-C) had a significant ($P<0.04$) effect on blastocyst formation of embryos co-cultured with CGs (Table 4). More embryos developed to the blastocyst stage after addition of 1 $\mu$g/ml Hb (34%) to the medium than after no addition (18%) ($P<0.02$). Addition of 10 $\mu$g/ml Hb also caused an increase ($P<0.07$) in the percentage reaching the blastocyst stage (27%). There was no significant difference between 1 and 10 $\mu$g/ml Hb in the percentage of blastocyst formation. In this experiment, the addition of Hb was found not to have a significant ($P>0.2$) effect on development to the 2-cell (77–81%), 8-cell (53–60%), 16-cell (40–52%), or morula (34–46%) stages.

TABLE 4

Results of Example 4: Effects of the Addition of Hemoglobin (Hb; 1 or
10 $\mu$g/ml) to mBECM-C Containing Fetal Bovine Serum (10%, v/v) on the
Pre-hatching Development of Embryos (95 per Group) Co-Cultured in
Groups with Granulosa Cells

| Hb Concentration ($\mu$g/ml) | No. of embryos cultured | Percent of Embryos Developed to: | | | | |
|---|---|---|---|---|---|---|
| | | 2-cell | >8-cell | 16-cell | Morula | Blastocyst |
| 0 | 95 | 77 | 55 | 40 | 34 | 18[a] |
| 1 | 95 | 81 | 60 | 52 | 46 | 34[b] |
| 10 | 95 | 78 | 53 | 43 | 41 | 27[ab] |

[a,b]Values with different superscripts are significantly different, $P < 0.05$.

Results, Example 5

In this experiment, the time of Hb addition was found to significantly ($P<0.05$) influence embryonic development to the 16-cell, morula, and blastocyst stages. As shown in Table 5, a higher (P<0.02) proportion of 16-cell embryos was obtained after Hb addition at 18 h post-insemination (43%) compared to controls (23–27%). More (P<0.07) morulae (33%) were obtained after Hb addition at 18 h post-insemination as compared with controls (17–22%). The proportion of blastocysts greatly (P<0.04) increased after addition of Hb at 18 or 60 h (24–29%) post-insemination compared to controls (13%). The ratios of blastocysts:morulae were 0.74, 1.00, 0.96, and 0.72 for Hb addition at 18, 60, 144, and 192 (i.e., no addition) h post-insemination. Hb addition was found to have no effect on development to the 2-cell (P>0.24) and 8-cell (P>0.06) stages.

Results, Example 7

Addition of Hb to mBECM-S was found to have no significant effect on the proportions of 8-cell embryos developing to each embryonic stage (P>0.09). As shown in Table 7, similar proportions of 8-cell embryos developed beyond the 8-cell (68–74%), 16-cell (44–56%), morula (26–28%), and blastocyst (8%) stages when embryos previously cultured to the 8-cell stage in the presence of Hb were then cultured singly in a chemically defined medium (mBECM-S).

TABLE 5

Results of Example 5: Effects of the Addition of Hemoglobin (Hb, 1 $\mu$g/ml) to mBECM-C Containing Fetal Bovine Serum (10%, v/v) at Different Times of Culture on the Pre-hatching Development of Inseminated Oocytes (104 per group) Co-cultured with Cumulus-Granulosa Cells (CGs)

| Hb addition at (hrs post-insemination) | Developmental stages at Hb addition | No. of oocytes cultured | \multicolumn{5}{c}{No and (%) of embryos developed to the} | Ratio of blastocysts to morulae |
|---|---|---|---|---|---|---|---|---|
| | | | 2-cell[b] | 8-cell[b] | 16-cell[b] | Morula[b] | Blastocyst[b] | |
| 18 | 1-cell | 104 | 76 (73) | 52 (50) | 45 (43)[c] | 34 (33)[c] | 25 (24)[c] | 0.74 |
| 60 | 8-cell | 104 | 67 (64) | 40 (38) | 35 (34)[c,d] | 30 (29)[c,d] | 30 (29)[c] | 1.00 |
| 144 | Morula | 103[a] | 64 (62) | 34 (33) | 28 (27)[c,d] | 23 (22)[c,d] | 22 (22)[c,d] | 0.96 |
| 192 (no addition) | — | 104 | 74 (71) | 37 (36) | 24 (23)[d] | 18 (17)[d] | 13 (13)[d] | 0.72 |

[a]One embryo developed to the 2-cell stage was cracked by dislodging from CGs.
[b]Development to the 2-cell, 8-cell, 16-cell, morula, and blastocyst stages was examined at 48, 60, 120, 144, and 192 hours post-insemination, respectively.
[c,d]Values with different superscripts within each column are significantly different, P < 0.05.

Results, Example 6

As shown in Table 6, Hb was not seen to promote the pre-hatching development of embryos cultured in the absence of CG. However, in the culture system containing CG, when Hb was added more (P<0.05) embryos developed to the 16-cell (51% vs. 30–34%; P<0.03), morula (40% vs. 20–27%; P<0.05) and blastocyst (33% vs. 16–19%; P<0.03) stages. Hb and CGs had no significant effect (P>0.4) on the development of embryos to the 2-cell (73–77%) and 8-cell stages (45–55%).

TABLE 6

Results of Example 6:
Effects of the Addition of Hemoglobin (1 $\mu$g/ml) to mBECM-C Containing Fetal Bovine Serum (10%, v/v) on the Pre-hatching Development of Embryos (93 per Group) Cultured in Groups in the Presence and Absence of Cumulus-Granulosa Cells (CG)

| | No. of embryos cultured | \multicolumn{5}{c}{Percent of Embryos Developed to:} |
|---|---|---|---|---|---|---|
| | | 2-cell | 8-cell | 16-cell | Morula | Blastocyst |
| negative control | 93 | 74 | 45 | 30[a] | 20[a] | 16[a] |
| Hb only | 93 | 73 | 52 | 34[a] | 27[ab] | 19[a] |
| Hb + CG | 93 | 77 | 55 | 51[b] | 40[b] | 33[b] |

[a,b]Values with different superscripts within each column are significantly different, P < 0.05.

TABLE 7

Results of Example 7: Effects of the Addition of Hb (1 $\mu$g/ml) to mBECM-C on Development of 8-Cell Embryos (100 per group) Derived from Cumulus-Granulosa Cell Coculture System Containing Hb

| Presence (+) or absence (−) of Hb in mBECM-S | Number of 8-cell embryos cultured | \multicolumn{4}{c}{Number of embryos developed to} |
|---|---|---|---|---|---|
| | | >8-cell[a] | 16-cell[a] | Morula[a] | Blastocyst[a] |
| + | 100 | 68 | 44 | 26 | 8 |
| − | 100 | 74 | 56 | 28 | 8 |

[a]Development beyond the 8-cell stage and to the 16-cell, morula, and blastocyst stages was examined at 96, 120, 144, and 192 hours post-insemination, respectively.

Discussion

We tested a number of medium supplements to establish a better culture medium for mammalian embryos. We found a significant increase in nitric oxide metabolites in developmentally arrested embryos. We discovered that the addition of an NO scavenger such as hemoglobin to a culture medium containing serum and co-cultured somatic cells promoted embryonic development to the blastocyst stage. Our results indicated that NO secreted from the cumulus granulosa cells inhibited the preimplantation development of IVF-derived embryos in co-culture systems.

These results raised further questions concerning the effect of Hb and the interactions between the embryotropic and embryotoxic effects of serum and co-culture cells in various kinds of culture media. We conducted further experiments to answer these questions. First, we investigated whether the promoting effect of Hb was repeatable at different times of year. Second, we tested alternative approaches to removing NO from a culture system: 1) adding an NO synthase inhibitor to the culture medium to directly inhibit NO production by co-cultured cells; and 2) using an NO scavenger to inactivate NO in the culture system.

Materials and Methods

EXAMPLES 8 AND 9
Media Composition (Examples 8 and 9)

The basic medium used for maturation of oocytes was tissue culture medium (TCM)-199 with Earle's salts, buffered with 25 mM HEPES (Gibco BRL, Grand Island, N.Y.) and supplemented with 10% (v/v) heat-inactivated fetal bovine serum (FBS; Hyclone Laboratories, Logan, Utah), 1 $\mu$g/ml estradiol-17$\beta$ (NOBL Laboratories, Sioux Center, Iowa), 3 $\mu$g/ml bovine FSH (NOBL Laboratories), 6 $\mu$g/ml bovine LH (NOBL Laboratories), and 25 $\mu$g/ml gentamycin (Sigma Chemical Co., St. Louis, Mo.). The basic medium used for treatment of spermatozoa and fertilization of oocytes was a modified Tyrode's medium (J. Parrish et al., Capacitation of bovine sperm by heparin. *Biol. Reprod.* 38:1171–1180 (1988)), supplemented with 0.25 mM sodium pyruvate (Gibco BRL), 6 mg/ml fatty acid (FA)-free BSA (No. A-6003, Sigma), 15 $\mu$g/ml calcium heparin from porcine intestinal mucosa (183 USP/mg; H-8398, Sigma), and 25 $\mu$g/ml gentamycin. Modified bovine embryo culture medium (mBECM) containing 10 $\mu$M $\beta$-mercaptoethanol was used for culture of embryos, as described in J. Lim et al., "Roles of growth factors in the development of bovine embryos fertilized in vitro and cultured singly in a defined medium," *Reprod. Fertil. Dev.*, 8:1199–1205 (1996). mBECM supplemented with 10% (v/v) FBS was used for co-culturing inseminated oocytes with CGC. Osmolarity of the medium was maintained within the range of 265–290 mOsm.

In vitro-maturation (IVM), IVF, and in vitro-culture (IVC) of oocytes (Examples 8 and 9)

All cumulus-oocyte complexes (COC) were collected in Madison, Wis. (BOMED, Inc.) and were shipped in 2 ml of maturation medium in a battery powered incubator via overnight express mail service. Oocytes matured during transit and arrived within 24 h after exposure to maturation medium, pre-equilibrated at 39° C. in 5% $CO_2$ in air. At 22 to 24 h after exposure to the medium, the COCs were inseminated in vitro as described in J. Lim et al., "Intracytoplasmic glutathione concentration and the role of $\beta$-mercaptoethanol in preimplantation development of bovine embryos," *Theriogenology*, 46:429–439 (1996). At 18 h post-insemination, COCs were cultured in groups (28–40 embryos) in a 4-well multidish (Nunc, Roskilde, Denmark) containing 0.8-ml of mBECM. Embryos were dislodged from CGC at 36 to 48 h post-insemination.

Experimental design (Examples 8 and 9)

In Example 8, bovine follicular oocytes were collected from November 1996 to May 1997, and matured and fertilized in culture. (Oocytes collected during summer and early fall were not used in this study, to avoid interference from environmental heat stress on in vitro survival of embryos.) IVF embryos were collected at 18 h post-insemination and cultured in mBECM supplemented with FBS (10%, v/v), to which 0 or 1$\mu$g/ml Hb (from bovine, mainly methemoglobin, H-2500, Sigma Co.) was added. Development of embryos to the 2-cell, 8-cell, 16-cell, morula, and blastocyst stages was monitored 48, 60, 120, 144 and 192 h post-insemination, respectively. As a supplemental experiment, some blastocysts in each treatment (20 or 28) were randomly collected, and the cell number of the blastocysts was counted by use of Hoechst stain 33342 and a fluorescent microscope (Diaphod, Nikkon, Tokyo, Japan). This experiment used 1675 embryos in 25 replicates, with IVF embryos randomly allotted among treatments.

In Example 9, IVF embryos were cultured in mBECM supplemented as follows: 1) no addition (control), 2) Hb (1 $\mu$g/ml), 3) Hb plus L-NAME (1 nM), and 4) Hb plus L-NAME (1000 nM). Embryonic development was evaluated up to 192 h post-insemination. A total of 384 oocytes were inseminated, and were randomly and equally allotted to 4 replicates.

Statistical analyses (Examples 8 and 9)

Embryos developed to the 2-cell, 8-cell, 16-cell, morula, and blastocyst stages at the pertinent observation times were individually scored '1' (developed). Embryos that had not developed to these stages at the same times were scored '0' (non-developed). Sums of the scores at each stage of development were evaluated by analysis of variance using a general linear model (PROC-GLM) in the SAS statistical programming package (1991). In Example 8, the combined effects of Hb addition and month of oocyte collection were first examined in a 2×7 factorial arrangement. Overall differences in embryonic development in Hb-free and Hb-containing culture systems were further evaluated. In Example 9, when each of the factors was found to be significant, the effects of Hb and L-NAME were compared by the least squares method. Differences were regarded as statistically significant where P values were less than 0.05.

Results, Example 8

A total of 1,675 oocytes inseminated in vitro were used to evaluate the effect of Hb on pre-hatching embryonic development. The least mean square number of embryos developed to each stage in all tested months is shown in Table 8. Significant (P<0.0024) effects of Hb addition and month were found in all parameters (Table 9). Monthly variations were highly significant (P<0.0023) in all developmental stages, and the effect of Hb addition was found in embryonic development at the 8-cell stage or higher (P<0.0459). Regardless of the month, formations of morulae (0.23–0.57 vs. 0.2–0.37) and blastocysts (0.20–0.4 vs. 0.17–0.32) were enhanced after Hb addition compared with control. However, interactions between Hb addition and month were not detected in any parameters except the first cleavage.

TABLE 8

Variations in pre-hatching development of bovine IVF-oocytes collected during different months and cultured in modified bovine embryo culture medium with or without hemoglobin (Hb, 1 µg/ml) following in vitro maturation and IVF

| Season (Month) | Addition (+) of Hb | Least square mean ± SE of embryos developed to | | | | |
|---|---|---|---|---|---|---|
| | | 2-cell | 8-cell | 16-cell | Morula | Blastocyst |
| November | + | 0.89 ± 0.07 | 0.71 ± 0.08 | 0.60 ± 0.08 | 0.57 ± 0.08 | 0.34 ± 0.07 |
| | − | 0.66 ± 0.04 | 0.44 ± 0.04 | 0.35 ± 0.04 | 0.31 ± 0.04 | 0.23 ± 0.04 |
| December | + | 0.79 ± 0.05 | 0.59 ± 0.05 | 0.53 ± 0.05 | 0.41 ± 0.05 | 0.36 ± 0.05 |
| | − | 0.80 ± 0.04 | 0.59 ± 0.04 | 0.40 ± 0.04 | 0.36 ± 0.04 | 0.27 ± 0.04 |
| January | + | 0.70 ± 0.04 | 0.45 ± 0.04 | 0.42 ± 0.04 | 0.32 ± 0.04 | 0.28 ± 0.04 |
| | − | 0.70 ± 0.03 | 0.42 ± 0.04 | 0.27 ± 0.04 | 0.21 ± 0.04 | 0.20 ± 0.03 |
| February | + | 0.77 ± 0.04 | 0.53 ± 0.04 | 0.44 ± 0.04 | 0.40 ± 0.04 | 0.35 ± 0.04 |
| | − | 0.80 ± 0.04 | 0.53 ± 0.04 | 0.42 ± 0.04 | 0.37 ± 0.04 | 0.27 ± 0.04 |
| March | + | 0.58 ± 0.05 | 0.40 ± 0.06 | 0.31 ± 0.06 | 0.23 ± 0.06 | 0.20 ± 0.05 |
| | − | 0.71 ± 0.05 | 0.39 ± 0.06 | 0.26 ± 0.06 | 0.20 ± 0.06 | 0.17 ± 0.05 |
| April | + | 0.70 ± 0.03 | 0.48 ± 0.03 | 0.39 ± 0.03 | 0.32 ± 0.03 | 0.25 ± 0.03 |
| | − | 0.67 ± 0.04 | 0.41 ± 0.05 | 0.34 ± 0.05 | 0.25 ± 0.05 | 0.21 ± 0.04 |
| May | + | 0.70 ± 0.05 | 0.60 ± 0.05 | 0.49 ± 0.05 | 0.44 ± 0.05 | 0.40 ± 0.05 |
| | − | 0.81 ± 0.05 | 0.60 ± 0.05 | 0.51 ± 0.05 | 0.41 ± 0.05 | 0.32 ± 0.05 |

TABLE 9

Analysis for monthly variation of hemoglobin effect on embryonic development from the data of Table 8.

| Parameter | Factor | DF | Square | F value | Pr > F |
|---|---|---|---|---|---|
| 2-cell embryo | Experimental model | 13 | 0.505 | 2.59 | 0.0015 |
| | Month | 6 | 0.667 | 3.42 | 0.0023 |
| | Hb addition | 1 | 0.001 | 0.00 | 0.9944 |
| | Interaction | 6 | 0.436 | 2.23 | 0.0377 |
| 8-cell embryo | Experimental Model | 13 | 0.717 | 2.91 | 0.0003 |
| | Month | 6 | 1.283 | 5.20 | 0.0001 |
| | Hb addition | 1 | 0.984 | 3.99 | 0.0459 |
| | Interaction | 6 | 0.314 | 1.27 | 0.2660 |
| 16-cell embryo | Experimental Model | 13 | 0.789 | 3.35 | 0.0001 |
| | Month | 6 | 1.098 | 4.66 | 0.0001 |
| | Hb addition | 1 | 2.558 | 10.87 | 0.0001 |
| | Interaction | 6 | 0.352 | 1.50 | 0.1753 |
| Morula | Experimental Model | 13 | 0.787 | 3.61 | 0.0001 |
| | Month | 6 | 1.348 | 6.19 | 0.0001 |
| | Hb addition | 1 | 2.265 | 10.39 | 0.0013 |
| | Interaction | 6 | 0.239 | 1.10 | 0.3622 |
| Blastocyst | Experimental Model | 13 | 0.4845 | 2.48 | 0.0024 |
| | Month | 6 | 0.6978 | 3.57 | 0.0016 |
| | Hb addition | 1 | 1.8041 | 9.23 | 0.0024 |
| | Interaction | 6 | 0.0328 | 0.17 | 0.9853 |

An overall comparison of embryonic development in all months is shown in Table 10. Embryonic development to the 8-cell (0.54 vs. 0.48, P<0.045), 16-cell (0.45 vs. 0.37, P<0.001), morula (0.39 vs. 0.31, P<0.001) and blastocyst (0.31 vs. 0.24, P<0.001) stages was significantly stimulated after addition of Hb as compared to control. However, no significant effect of Hb addition was found (P>0.73) in development to the 2-cell stage. In a supplemental experiment, the number of blastocyst cells 8 days after insemination did not significantly change after addition of Hb to the culture medium (128.6±7.1 vs. 124.2±8.4).

TABLE 10

Overall comparison of the pre-hatching development[a] of bovine IVF oocytes cultured in modified bovine embryo culture medium with or without hemoglobin (Hb, 1 µg/ml)

| Addition of | No. of Embryos Cultured | Number (least square mean ± SE) of embryos | | | | |
|---|---|---|---|---|---|---|
| | | 2-cell | 8-cell | 16-cell | Morula | Blastocyst |
| — | 844 | 621 (0.73 ± 0.02) | 409 (0.48 ± 0.02)[b] | 308 (0.37 ± 0.02)[b] | 256 (0.31 ± 0.02)[b] | 203 (0.24 ± 0.02)[b] |
| Hb, 1 µg/ml | 831 | 601 (0.73 ± 0.02) | 427 (0.54 ± 0.02)[c] | 358 (0.45 ± 0.02)[c] | 300 (0.39 ± 0.02)[c] | 251 (0.31 ± 0.02)[c] |

[a]Pre-hatching development to the 2-cell, 8-cell, 16-cell, morula and blastocyst stages was monitored at 48, 60, 120, 144 and 192 hours post-insemination, respectively.
[bc]Different superscripts in each column are significantly different, P < 0.05 in the 8-cell, P < 0.001 in the 16-cell, P < 0.001 in the morula, and P < 0.002 in the blastocyst stages.

Results, Example 9

As shown in Table 11, a significant effect was seen in embryonic development at the 16-cell (P<0.0753) and blastocyst (P<0.0696) stages. More (P<0.02) embryos developed to the 16-cell (0.489 vs. 0.323; P<0.02) and blastocyst (0.312 vs. 0.167; P<0.018) stages after addition of Hb to mBECM than did the controls. Addition of L-NAME to culture medium containing Hb did not further stimulate (P>0.07) embryonic development to the blastocyst stage.

co-culture, and that continuous removal of NO from a co-culture system is essential to optimize pre-hatching development.

The scavenging action of Hb for NO limits diffusion of potentially toxic amounts of NO into developing embryos. Embryos themselves do not appear to produce toxic amounts of NO, as indicated by the fact that adding Hb to embryos cultured in a defined medium in the absence of CGs was not found to be beneficial. (Tables 6 and 7). De novo production

TABLE 11

Effects of addition of Nω-nitro-L-arginine methyl ester (L-NAME, 1 or 1000 nM) on pre-hatching development of bovine embryos cultured in modified bovine embryo culture medium containing fetal calf serum (10%, v/v) and hemoglobin (Hb, 1 μg/ml)[a]

| Presence (+) or absence (−) of | | Number of embryos cultured | Number (least square mean) of embryos developed to | | | | |
|---|---|---|---|---|---|---|---|
| Hb | L-NAME (nM) | | 2-cell | 8-cell | 16-cell | Morula | Blastocyst |
| − | − | 96 | 68 (0.708) | 43 (0.448) | 31 (0.323)[b] | 26 (0.271) | 16 (0.167)[b] |
| + | − | 96 | 68 (0.708) | 54 (0.563) | 47 (0.489)[c] | 35 (0.365) | 30 (0.313)[c] |
| + | + (1) | 96 | 78 (0.813) | 60 (0.625) | 46 (0.479)[c] | 38 (0.396) | 26 (0.271)[bc] |
| + | + (1000) | 96 | 70 (0.729) | 50 (0.521) | 40 (0.416)[bc] | 28 (0.292) | 19 (0.198)[bc] |

[a]Embryonic development to the 2-cell, 8-cell, 16-cell, morula and blastocyst stages was monitored at 48, 60, 120, 144 and 192 hours post-insemination, respectively.
[b,c]Different superscripts in each column are significantly different, P < 0.03.

Discussion

The results of Examples 1 and 2 clearly demonstrated that addition of a spontaneous NO donor inhibited bovine embryonic development in vitro at concentrations as low as 0.008 mM in both mBECM-C and mBECM-S. In Example 2, a single defined culture system, in which embryos were cultured individually, was used to evaluate the inhibitory effects of NO on embryonic development. We found that NO directly affected embryos cultured in vitro. These results were supported by the finding in Example 3 that developmentally arrested embryos contained a higher concentration of NO metabolites than did developing embryos at 144 h post-insemination. A comparable difference between developing and arrested embryos was not seen at 48 h post-insemination (Table 3). Compared with other cell types, embryos developing in vitro appeared to be sensitive to very low concentrations (~0.0016 mM) of NO. For example, in other studies in our laboratory bovine luteal cells cultured for 24 h in the presence of NO in similar concentrations produced normal amounts of progesterone, with no changes in viability (data not shown).

The results of Examples 4 and 5 demonstrated the promoting action of Hb on pre-hatching embryonic development. The results of Example 4 (Table 4) showed that Hb supported the transition of embryos from the morula to the blastocyst stage. The results of Example 5 (Table 5), in which Hb was added at different stages of development, showed that Hb was also beneficial when added at earlier stages. The results of Example 5, showing significant differences in the proportions of 16-cell embryos, morulae, and blastocysts formed after addition of Hb at the 1-cell stage, showed that Hb had a beneficial effect on early development, before the morula stage. However, when we compared the development of morulae to the blastocyst stage, addition of Hb at the 1-cell stage did not stimulate the conversion of morulae to blastocysts (Table 5). In contrast, addition of Hb at either the 8-cell or morula stage resulted in the conversion of nearly all morulae into blastocysts. These results led us to conclude that embryonic development is continuously affected by newly-synthesized NO during in vitro co-culture, and that continuous removal of NO from a co-culture system is essential to optimize pre-hatching development.

of the metabolites in control media containing L-arginine could not be detected after incubation for periods up to 174 h.

The inhibitory action of NO on pre-hatching embryonic development was distinct, even in the presence of embryotropic substances such as PDGF, TGF, AA, GSH and ME (Table 2). Indeed, the embryotoxic effect of NO may partially neutralize the beneficial effects of serum and co-cultured reproductive tissue cells on embryonic development. Elimination of NO from the culture medium will help to optimize the effect of embryotropins in the culture system. While frequent changes of the culture medium could also help remove embryotoxic substances from the culture system, such frequent changes of medium would also remove beneficial embryotropic substances secreted by the embryos or somatic helper cells. Removal of NO from the culture medium by the addition of an NO scavenger such as Hb, or by a blocker of NO synthase such as L-NAME is more advantageous.

While hemoglobin is preferred NO scavenger for use in this invention, other NO scavengers and NO synthase blockers may be used in this invention as well.

Examples of NO scavengers include astaxanthin; carboxy-PTIO: (2-(4-carboxyphenyl)-4,4,5,5-tetramethyl-imidazolino-1-oxyl-3-oxide); cyanidin chloride; pelargonidin chloride; PTIO; rutin-trihydrate; α-tocopherol; α-tocopherol acetate.

Examples of nitric oxide synthase blockers (inhibitors of nNOS, eNOS, and iNOS) include L-NAME; L-NMEA (N-monoethyl-L-arginine monoacetate); L-NMMA ($N^G$-monomethyl-L-arginine monoacetate); D-NMMA ($N^G$-monomethyl-D-arginine monoacetate); L-NMMHA ($N^G$-monomethyl-L-homoarginine monoacetate); α-tocopherol; and polyclonal or monoclonal antibodies to nitric oxide synthases.

Other compounds are known in the art to act as NO scavengers or nitric oxide synthase inhibitors. Additional examples may be found in the catalog of Alexis Biochemicals, 6181 Cornerstone Court East, Suites 102–104, San Diego, Calif. 92121.

Unless context clearly indicates otherwise, as used in the specification and claims, a "nitric oxide inhibitor" may be either a nitric oxide scavenger (a compound or composition that removes nitric oxide from a system) or a nitric oxide synthase blocker (a compound or composition that blocks the action of a nitric oxide synthase).

Systems, other than those for culturing oocytes and embryos, where removal of NO from the cell culture medium through the present invention may be advantageous include those for epithelial cells such as oviduct epithelial cells, endothelial cells, fibroblasts, cumulus cells, and endometrial cells.

In these experiments, a significant proportion (0.31±0.02) of bovine IVF embryos developed to the blastocyst stage after the addition of Hb to mBECM as compared to controls. Consistency in the promoting effect of Hb was noted throughout the entire 7-month experimental period, especially in development beyond the 8-cell level. The morphological normality of blastocysts from Hb-containing culture systems was confirmed by the supplemental experiment of counting blastocyst cell numbers.

The finding of an inhibitory role of NO in early development is confirmed by our experimental findings that the presence of an NO donor, sodium nitroprusside, completely blocked pre-hatched embryonic development even before implantation.

We observed a substantial monthly change in the developmental competence of IVF embryos during the period of Examples 8 and 9. This variation affected pre-hatch development from the first cleavage to blastocyst formation (Table 8). However, the effect of Hb addition on embryonic development was found to be independent of monthly variation, except at the first cleavage. Although blastocyst formation varied by month, the addition of Hb to the culture media consistently stimulated the development of IVF embryos to the blastocyst stage, regardless of month.

In the presence of Hb in the embryo culture system, addition of an NO synthesis inhibitor, L-NAME, did not further augment the promoting action of Hb (Table 11).

When the novel method is used in human in vitro fertilization procedures, it will usually be preferable either to use hemoglobin derived from known disease-free laboratory animals, or to use hemoglobin extracted from the mother's (or surrogate's) own blood, or NO inhibitors from known disease-free sources, to reduce the likelihood of infections from blood-born pathogens.

As used in the claims, "free" hemoglobin refers to hemoglobin that is not contained within erythrocytes; for example, hemoglobin that has been separated (or substantially separated) from erythrocytes through means known in the art, or hemoglobin that has been produced by molecular cloning (for example in *E. coli* or yeast).

As used in the claims, an "effective amount" of a nitric oxide inhibitor is an amount that reduces the concentration of nitric oxide present in a culture medium to a degree that produces a statistically significant improvement in the maintenance, growth, development, or survival rates of cells in vitro, as compared to the rates obtained in an otherwise identical culture medium that lacks the nitric oxide inhibitor.

The complete disclosures of all references cited in this specification are hereby incorporated by reference. Also incorporated by reference are the complete disclosures of each of the following reports of the inventors' own work, none of which is prior art to the present patent application: J. Lim et al., "Hemoglobin Enhances Pre-Hatching Development of Bovine Oocytes Matured and Fertilized In Vitro by Scavenging Nitric Oxide," Abstract of Presentation at 30th Annual Meeting of the Society for the Study of Reproduction (Portland, Oreg., August 1997); W. Hansel et al., "Use of Hemoglobin (Hb) to Improve Development of Bovine IVF Embryos in a Cumulus-Granulosa Cell Co-Culture System," Abstract of Presentation at Meeting of International Embryo Transfer Society (Boston, January 1998); J. Lim et al., "Improved Development of In Vitro-Derived Bovine Embryos by Use of a Nitric Oxide Scavenger in a Cumulus-Granulosa Cell Coculture System," Molec. Repro. & Dev., 50:45–53 (1998). In the event of an otherwise irreconcilable conflict, however, the present specification shall control.

We claim:

1. A method for promoting the growth and development of a mammalian oocyte or embryo; said method comprising growing the oocyte or embryo in a culture medium comprising nutrients conducive to the growth of mammalian cells in vitro, an effective amount of a nitric oxide inhibitor, and helper cells that promote the maintenance, growth, or development of a mammalian oocyte or embryo.

2. A method as recited in claim 1, wherein the helper cells comprise cumulus-granulosa cells.

3. A method as recited in claim 1, wherein the nitric oxide inhibitor comprises hemoglobin.

4. A method as recited in claim 1, wherein the nitric oxide inhibitor comprises free hemoglobin.

5. A method as recited in claim 1, wherein the cell or cells comprise a bovine oocyte or embryo.

6. A method as recited in claim 1, wherein the cell or cells comprise a human oocyte or embryo.

7. A method as recited in claim 6, wherein the cell or cells comprise a human embryo; additionally comprising the step of implanting the embryo into a woman's uterus following said growing in the culture medium; wherein the nitric oxide inhibitor comprises free hemoglobin derived from the woman's own erythrocytes.

8. A method for promoting the growth and development of a mammalian cell or cells, wherein the cell or cells are selected from the group consisting of mammalian epithelial cells, endothelial cells, fibroblasts, cumulus cells, and endometrial cells; said method comprising growing the cell or cells in a culture medium comprising nutrients conducive to the growth of mammalian cells in vitro, and an effective amount of a nitric oxide inhibitor.

9. A method as recited in claim 8, wherein the nitric oxide inhibitor comprises hemoglobin.

10. A method as recited in claim 8, wherein the nitric oxide inhibitor comprises free hemoglobin.

* * * * *